(12) United States Patent
Dubois

(10) Patent No.: US 8,829,223 B2
(45) Date of Patent: Sep. 9, 2014

(54) METHOD FOR THE SYNTHESIS OF ACRYLONITRILE FROM GLYCEROL

(75) Inventor: Jean-Luc Dubois, Millery (FR)

(73) Assignee: Arkema France, Colombes (FR)

( * ) Notice: Subject to any disclaimer, the term of this patent is extended or adjusted under 35 U.S.C. 154(b) by 57 days.

(21) Appl. No.: 12/527,352

(22) PCT Filed: Feb. 18, 2008

(86) PCT No.: PCT/FR2008/050261

§ 371 (c)(1),
(2), (4) Date: Nov. 5, 2009

(87) PCT Pub. No.: WO2008/113927

PCT Pub. Date: Sep. 25, 2008

(65) Prior Publication Data

US 2010/0048850 A1    Feb. 25, 2010

(30) Foreign Application Priority Data

Feb. 16, 2007   (FR) ...................................... 07 53293

(51) Int. Cl.
C07C 253/24      (2006.01)

(52) U.S. Cl.
CPC ................................... *C07C 253/24* (2013.01)
USPC ......................................... 558/316; 558/319

(58) Field of Classification Search
CPC .................................................... C07C 253/24
USPC ................................................ 558/316, 319
See application file for complete search history.

(56) References Cited

U.S. PATENT DOCUMENTS

| | | | | |
|---|---|---|---|---|
| 1,916,743 A | * | 7/1933 | Schwenk et al. | 568/486 |
| 4,138,430 A | * | 2/1979 | Stiles et al. | 558/316 |
| 5,387,720 A | * | 2/1995 | Neher et al. | 568/486 |
| 6,204,407 B1 | * | 3/2001 | Godbole et al. | 558/319 |

FOREIGN PATENT DOCUMENTS

| | | | |
|---|---|---|---|
| BE | 628287 | | 8/1963 |
| EP | 558424 | | 9/1993 |
| GB | 709337 | | 12/1951 |
| GB | 897226 | | 5/1962 |
| WO | WO 2006/087083 | * | 8/2006 |

OTHER PUBLICATIONS

Albonetti et al. (Catalysis Letters 45 (1997) 119-123).*
Ott et al. (Green Chem., 2006, 8, 214-220).*
Oka, Journal of Applied Biotechnology, vol. 25, pp. 663-670 (1975).
Leete et al., Journal of the American Chemical Society, vol. 98, pp. 6321-6325 (1976).
Tanabe et al., Studies in Surface Science and Catalysis, vol. 51, chapters 1 and 2 (1989).
J.E. Germain et coll. Bull. Soc. Chim., No. 3-4, pp. 731-734 (1975).
M. Cathala and J.E. Germain in Bull. Chem. Soc., No. 6, pp. 2167-2174 (1971).
Bartholomew et al., Fundamentals of Industrial Catalytic Processes, 2nd Edition, Wiley Interscience, pp. 604-609 (2006).
International Search Report for International Application No. PCT/FR2008/050261, mailed Aug. 8, 2008.
Written Opinion for International Application No. PCT/FR2008/050261, mailed Aug. 8, 2008.

* cited by examiner

*Primary Examiner* — Robert Havlin
(74) *Attorney, Agent, or Firm* — Hunton & Williams LLP

(57) ABSTRACT

The invention relates to a novel way to synthesize acrylonitrile from a renewable raw material and more particularly relates to a method for producing acrylonitrile by the ammoxidation of glycerol in gaseous phase. The method can be implemented in a single step, or the glycerol can be previously submitted to a dehydration step. The acrylonitrile thus obtained meets the requirements of green chemistry.

12 Claims, 2 Drawing Sheets

METHOD FOR THE SYNTHESIS OF ACRYLONITRILE FROM GLYCEROL

CROSS-REFERENCE TO RELATED APPLICATIONS

This application is the U.S. National Phase of International Application No. PCT/FR2008/050261, filed Feb. 18, 2008, which claims the benefit of French Application No. FR 0753293, filed Feb. 16, 2007, the disclosure of each of which is incorporated herein by reference in its entirety.

FIELD OF THE INVENTION

The present invention relates to a new way of synthesizing acrylonitrile from a renewable raw material and one subject of the present invention is more particularly a method of synthesizing acrylonitrile from glycerol.

BACKGROUND

The current industrial production of acrylonitrile is based mainly on the Sohio process dating from 1957. This process consists of a catalytic oxidation, in the gas phase, of propylene by air in the presence of ammonia, a reaction known under the name of ammoxidation. The reaction is the following:

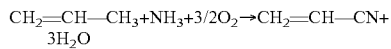

$$CH_2=CH-CH_3 + NH_3 + 3/2 O_2 \rightarrow CH_2=CH-CN + 3H_2O$$

The reaction is carried out in a fluidized-bed reactor, at a temperature generally between 400° C. and 500° C., and preferably from 420° C. to 450° C. for the most modern catalysts, under a pressure which may range from 20 kPa to 300 kPa, and more often from 150 kPa to 300 kPa. Various catalysts are used, such as complexes based on bismuth, or bismuth molybdate, or mixed molybdates of iron and of bismuth, or iron antimonate, or phosphomolybdate, or antimony-uranium combinations. Typically, a catalyst optimized for this process has a formulation $(K, Cs)_{0.1}(Ni, Mg, Mn)_{7.5}(Fe, Cr)_{2.3}Bi_{0.5}Mo_{12}Ox$ supported on 50 wt % of silica. It is thus possible to obtain around 1 to 1.1 kg of acrylonitrile per kg of propylene (reference: "Fundamentals of Industrial Catalytic Processes", C. H. Bartholomew, R. J. Farrauto, $2^{nd}$ Edition, Wiley Interscience, pages 604 to 609). This process has however numerous drawbacks.

The acrylonitrile obtained by ammoxidation of propylene contains impurities and byproducts that it is advisable to separate and that are not always reusable. The main byproducts are, in particular, hydrocyanic acid (HCN), acetonitrile ($CH_3CN$) and oxides of carbon. They result from the breaking of the C—C bond of propylene during the ammoxidation reaction carried out at high temperature and in the presence of very active catalysts. Hydrocyanic acid, after extraction and purification, may be used in processes for the synthesis of methyl methacrylate for example. On the other hand, acetonitrile, considering its limited applications, is generally destroyed. It therefore appears particularly advantageous to be able to use a different raw material, which by its nature will result in the desired product via a different reaction mechanism, and that generates less byproducts.

The ammoxidation reaction of propylene is strongly exothermic and consequently requires reactor technologies that make it possible to efficiently discharge the heat of reaction, such as for example multitubular reactors or fluidized beds. Due to the high risks of runaway linked to the exothermicity of the reaction, diluted streams are used, in particular use is generally made of a propylene/air/ammonia mixture in which the propylene only represents a few %. In this configuration, the reactor is sized as a function of the total amount of gas in the installation, and therefore over-sized with respect to the amount of the propylene reactant, which leads to a cost premium for the reactor.

The cost of the installation is also proportional to the amount of heat which must be exchanged in the process. It is therefore essential to minimize the heat losses by reducing the size of the units. It would therefore be particularly advantageous to be able to produce acrylonitrile according to a process that makes it possible to have partial pressures of reactants and products that are much higher than in the conventional case of the ammoxidation of propylene.

Furthermore, the current process for ammoxidation of propylene uses air as an oxidizing agent, thus supplying the inert gases (nitrogen) which the process needs. In a process with higher partial pressures of the reactants, it becomes possible to consider high-concentration oxygen, or oxygen-enriched air as an oxidizing agent. Air is often considered as a free reactant whereas oxygen is commercially available. However, the air must be purified and compressed in order to be used, which requires not only an investment in a compressor, but also variable electricity costs; whereas oxygen is available under pressure and with high qualities. The use of oxygen may then permit substantial reductions in investment in the industrial unit, but also in operating costs in certain cases.

Other routes for synthesizing acrylonitrile by an ammoxidation reaction are proposed in the prior art, especially starting from aldehydes, more particularly from acrolein, from an alkane such as propane, or from alcohols.

Patent GB 709 337 by Distillers describes a process for preparing acrylonitrile by ammoxidation of acrolein, used alone or as a mixture with the corresponding alcohol (allyl alcohol) or the corresponding acetal. The preferred catalysts are chosen from molybdenum-based catalysts capable of catalyzing the oxidation reaction of benzene to maleic anhydride or of naphthalene to phthalic anhydride. Yields between 25% and 60% are obtained.

In its improvement patent GB 897 226, Distillers obtains yields of acrylonitrile greater than 70% with respect to acrolein, by using, as catalysts, compounds based on antimony, tin and oxygen. The reaction may be carried out in the presence of an inert gas, such as nitrogen, water vapor, carbon dioxide or propane, butane or isobutane.

Patent BE 628 287 describes as process for the ammoxidation of acrolein that makes it possible to produce acrylonitrile with yields greater than 87% with an arsenic-based catalyst and a large proportion of water vapor as diluent.

Patent EP 558 424 describes a process for the ammoxidation of propane in the presence of a catalyst comprising vanadium, antimony and at least one metal chosen from iron, gallium or indium. Acrylonitrile selectivities which may reach more than 70% are obtained.

U.S. Pat. No. 4,138,430 describes the ammoxidation of n-propanol. The reaction is carried out in the presence of oxygen and ammonia by passing the gas stream successively over two catalyst beds: a first catalyst bed composed of boron phosphate, coprecipitated silica/alumina or coprecipitated alumina/tungsten oxide, over which the dehydration reaction of propanol to olefin is carried out and a second catalyst bed, that carries out the ammoxidation reaction of the olefin, composed of mixed oxides of Fe, Co, Ni, Bi, P, Mo and K, mixed oxides of Fe, Co, W, Bi, Mo and Mg, mixed oxides of Sb and U, bismuth molybdate or bismuth phosphomolybdate, or a mixture of these compounds. The two steps of the process are carried out at the same temperature, mainly at a very high temperature of more than 400° C. The advantage of the process lies in the combination of the endothermic dehydration and the exothermic ammoxidation, which allows a better control of the temperature. However, the acrylonitrile yields are not very high, and the proportion of byproducts such as acetonitrile, propionitrile and carbon oxides is high.

More generally, the ammoxidation reaction of propylene, of aldehydes such as acrolein, of ketones or of alcohols such as propanol or isopropanol has been the subject of many fundamental studies for determining the reaction mechanisms involved, or for studying the effect of various parameters, such as the nature of the catalyst or presence of water vapor as a diluent.

Mention may especially be made of the article by H. Oka et coll. in J. Appl. Chem. Biotechnol. (1975), 25, p. 663-670, relating to the ammoxidation of acrolein, which concludes that this reaction would be 1000 times faster than the ammoxidation of propylene, assuming that the reaction can be in a chemical regime at 400° C.

M. Cathala and J. E. Germain in Bull. Chem. Soc. No. 6, 1971, p. 2167-2174 studied the ammoxidation of acrolein at 460° C. over a Bi—Mo—O catalyst, which results in an acrylonitrile selectivity of 87%. According to the authors, the selectivity of the reaction starting from acrolein is higher than when starting from propylene over the same catalysts.

In the article in Bull. Soc. Chim. No. 3-4, (1975), p. 731-734, J. E. Germain et coll. compared the ammoxidation of propylene and of acrolein over an Sn—Sb—Fe—O type catalyst at about 450° C., with or without water vapor.

The ammoxidation of the alcohols isopropanol and n-propanol is itself compared in Bull. Soc. Chim. No. 5-6, (1979), p. 173-178. The ammoxidation of isopropanol at 460° C. over a Bi—Mo—O catalyst results in propylene as an initial product that gives, at high contact times, $CO=CO_2$, acetonitrile and acrylonitrile. But the nitrile selectivity is very different from that observed in the ammoxidation of propylene, thus the maximum conversion to acrylonitrile from isopropanol is only 17%. Over an Sn—Sb—O catalyst, the primary product is mainly acetone which leads to acetonitrile predominantly. Over the same catalyst, in the case of the ammoxidation of n-propanol, the primary product is n-propanaldehyde and not acetone. A notable difference in this case is also the absence of propylene. At a conversion close to 100%, the yield of acrylonitrile is only 7.5%.

SUMMARY OF THE INVENTION

The applicant company has now surprisingly discovered that it is possible to obtain acrylonitrile by ammoxidation of a renewable raw material, such as glycerol.

Glycerol is derived from the methanolysis of vegetable oils at the same time as the methyl esters, which are themselves used in particular as fuels in diesel and domestic fuel oil (D. Ballerini and G. Hillion, L'actualite chimique, November-December 2002, pages 64-69). This is a natural product that enjoys a "green" aura; it is available in a large amount and can be stored and transported without difficulty.

A process for producing acrylonitrile directly from glycerol is therefore particularly advantageous since it is not dependent on a raw material of fossil origin, such as propylene, but uses a renewable raw material. A renewable raw material is a natural, animal or plant resource, the stock of which may be regenerated over a short period on the human scale. It is necessary, in particular, that this stock can be renewed as quickly as it is consumed.

Indeed, unlike materials derived from fossil materials, materials composed of renewable raw materials contain $^{14}C$.

All the samples of carbon taken from living organisms (animals or plants) are in fact a mixture of three isotopes: $^{12}C$ (representing ~98.892%), $^{13}C$ (~1.108%) and $^{14}C$ (traces: $1.2\times10^{-12}$%). The $^{14}C/^{12}C$ ratio of living tissues is identical to that of the atmosphere. In the environment, $^{14}C$ exists in two main forms: in inorganic form, that is to say in the form of carbon dioxide ($CO_2$) and in organic form, that is to say in the form of carbon integrated in organic molecules.

In a living organism, the $^{14}C/^{12}C$ ratio is kept constant by the metabolism since the carbon is continually exchanged with the environment. Since the proportion of $^{14}C$ is substantially constant in the atmosphere, it is the same in the organism, as long as it is living, since it absorbs $^{14}C$ as it absorbs $^{12}C$. The average $^{14}C/^{12}C$ ratio is around $1.2\times10^{-12}$.

$^{12}C$ is stable, that is to say that the number of $^{12}C$ atoms in a given sample is constant over time. $^{14}C$, itself, is radioactive (each gram of carbon from a living being contains enough $^{14}C$ isotope to give 13.6 disintegrations per minute) and the number of such atoms in a sample decreases over time (t) according to the law:

$$n = no \exp(-at)$$

in which:
no is the number of $^{14}C$ at the start (at the death of the creature, animal or plant);
n is the number of $^{14}C$ atoms remaining at the end of time t; and
a is the disintegration constant (or radioactive constant); it is linked to the half-life.

The half-life (or period) is the duration at the end of which any number of radioactive nuclei or of unstable particles of a given species is reduced by half by disintegration; the half-life $T_{1/2}$ is connected to the disintegration constant a by the formula $aT_{1/2} = \ln 2$. The half-life of $^{14}C$ is equal to 5730 years.

Considering the half-life ($T_{1/2}$) of $^{14}C$, the content of $^{14}C$ is substantially constant from the extraction of the plant oil from which the glycerol is derived, up to the manufacture of the acrylonitrile and even up to the end of its use.

The acrylonitrile obtained from glycerol is composed of 100% organic carbon derived from a renewable resource, that is to say that it contains around $10^{-10}$% by weight of $^{14}C$ of the total mass of carbon, which could be certified by determining the content of $^{14}C$ according to one of the methods described in the standard ASTM D6866-06 or in the standard ASTM D 7026-04, especially according to the mass spectrometry or liquid scintillation spectrometry methods described in the standard ASTM D8866-06. These methods measure the $^{14}C/^{12}C$ ratio of a sample and compare it to the $^{14}C/^{12}C$ ratio of a reference sample of 100% renewable origin, in order to give a relative percentage of C of renewable origin in the sample.

Such a process therefore meets the criteria associated with the novel concept of "green chemistry", within a more global context of sustainable development.

Another advantage of this process lies in the fact that it generates fewer impurities, the ammoxidation reaction mechanism being different from that of propylene. Furthermore, since the glycerol raw material is already partially oxidized, its conversion to acrylonitrile is less exothermic than the ammoxidation of propylene, and consequently it is possible to carry out the synthesis in reactors of suitable size, with high partial pressures of the reactants, while limiting the risks associated with this synthesis.

One objective of the present invention is therefore to respond to the concerns of sustainable development while overcoming the drawbacks of the current processes.

One subject of the present invention is therefore a process for manufacturing acrylonitrile by an ammoxidation reaction of glycerol in the gas phase.

DETAILED DESCRIPTION OF PREFERRED EMBODIMENTS

Figure 1:
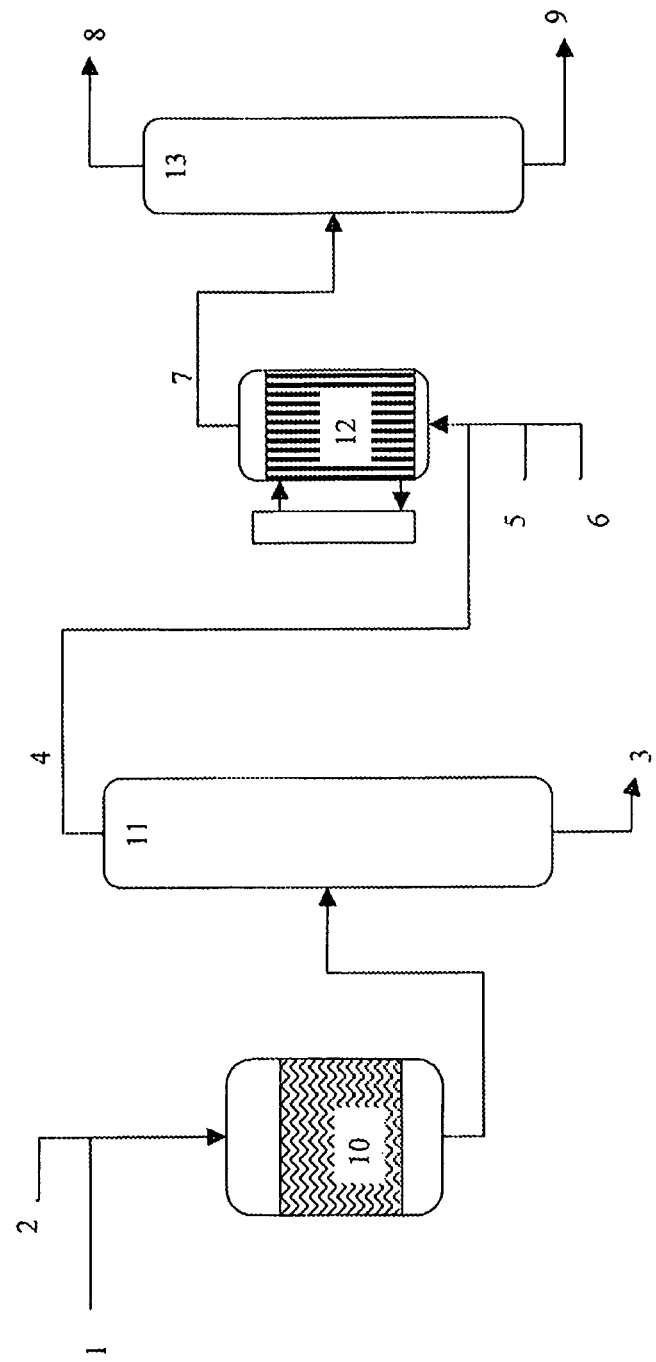
FIG. 1 is a schematic of a process for the manufacture of acrylonitrile comprising the dehydration of glycerol to form acrolein, partial condensation, and then the ammoxidation of acrolein to acrylonitrile.

The reaction mechanism is the following:

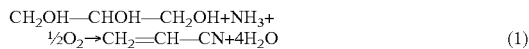

$$CH_2OH\text{—}CHOH\text{—}CH_2OH+NH_3+\tfrac{1}{2}O_2 \rightarrow CH_2\text{=}CH\text{—}CN+4H_2O \quad (1)$$

According to the present invention, the glycerol is reacted in the vapor phase with ammonia and oxygen in the presence of an acid catalyst, according to a single-step process.

The glycerol is used pure, or in the form of a concentrated or dilute aqueous solution. Advantageously, it is possible to use an aqueous solution of glycerol having a concentration ranging from 10% to 100% by weight. The concentration must not be too high in order to avoid parasitic reactions such as the formation of glycerol ethers or reactions between the acrylonitrile produced and the glycerol. Moreover, the glycerol solution must not be too dilute due to the energy cost induced by the evaporation of the aqueous solution of glycerol. The water vapor originating from the aqueous glycerol solution may vary within broad limits, but for a good implementation of the process according to the invention, the content of reaction gas, defined as being the glycerol/ammonia/oxygen sum, is preferably at least 2%, more particularly at least 4%, in the mixture including the water vapor and the inert gases, including nitrogen from the air when the latter is used as an oxidizing agent.

It is possible to use diluent gases that are inert under the reaction conditions such as helium, nitrogen or argon.

Within the reaction gas, the respective contents of glycerol, ammonia and oxygen may vary within broad limits.

The ammonia/glycerol molar ratio may vary between 1 and 1.5, and preferably between 1 and 1.2 and the oxygen/glycerol molar ratio may vary between 0.5 and 10 and preferably between 0.5 and 7.

The reaction temperature is, in general, between 280° C. and 550° C. and, preferably, between 400° C. and 500° C.

The total pressure of the reaction mixture may be greater than or equal to atmospheric pressure. It is generally between 1 and 5 bar and, preferably, between 1 and 4 bar.

The catalyst used in the process for ammoxidation of glycerol is an acid catalyst which is not saturated with ammonia at the reaction temperature. The catalyst may comprise one or more mixed oxides chosen for example from molybdenum, bismuth, iron, antimony, tin, vanadium, tungsten, antimony, zirconium, titanium, chromium, nickel, aluminum, phosphorus or gallium.

A person skilled in the art will be able to determine the compromise between the temperature, the gas flow rate and the precise nature of the catalyst used and the various other parameters of the reaction in order to obtain a good productivity.

According to one embodiment of the invention, the reaction is carried out in a single reactor, that is to say according to a direct ammoxidation of the glycerol where all the individual steps take place in one and the same reactor. Any device suitable for ammoxidation or oxidation reactions in the vapor phase may be used. The process may be carried out in continuous mode or in batch mode, using a fixed bed, a fluidized bed, a circulating bed, a plate heat exchanger with a modular arrangement of the catalyst, a microstructured reactor or a millistructured reactor.

According to one preferred embodiment of the invention, the glycerol is first subjected to a step of dehydration to acrolein, the reaction mechanism implementing the following two consecutive reactions:

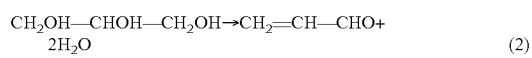

$$CH_2OH\text{—}CHOH\text{—}CH_2OH \rightarrow CH_2\text{=}CH\text{—}CHO+2H_2O \quad (2)$$

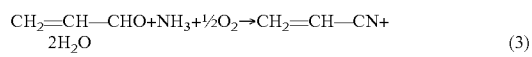

$$CH_2\text{=}CH\text{—}CHO+NH_3+\tfrac{1}{2}O_2 \rightarrow CH_2\text{=}CH\text{—}CN+2H_2O \quad (3)$$

In this case, the reaction is carried out by using two catalysts in series, an acid first catalyst that makes it possible to carry out the dehydration reaction of glycerol to acrolein and a second catalyst for the ammoxidation of the acrolein.

In this embodiment, the ammoxidation of the acrolein is advantageously carried out without intermediate purification of the acrolein and therefore as a mixture with the byproducts derived from the glycerol dehydration step, such as acetaldehyde or propanaldehyde. Indeed, the light aldehydes are converted to nitriles, preferably unsaturated nitriles, simultaneously in the ammoxidation step.

Furthermore, the dehydration of glycerol stoichiometrically produces two molecules of water. Therefore, the acrolein produced is naturally diluted in water vapor, all the more so when the glycerol is diluted in water. When the ammonia and oxygen necessary for the ammoxidation reaction are added, the reaction may be carried out in a concentrated reactant medium while remaining outside of the explosive limits. Under these conditions of a highly concentrated medium, it is possible to economically recycle the reactants which have not reacted or that have been insufficiently converted.

According to one particular embodiment, the two steps of the process are carried out at the same temperature, preferably between 400° C. and 500° C.

According to another embodiment, the two steps of the process are carried out at different temperatures, thus enabling the optimization of each of the two reactions, in terms of efficiency of the catalyst used and limitation of byproducts, such as the degradation products of glycerol at high temperature.

The glycerol dehydration step is carried out in the gas phase in the presence of a catalyst, at a temperature ranging from 150° C. to 500° C., preferably between 250° C. and 350° C., and a pressure between 1 and 5 bar.

The catalysts which are suitable are homogeneous or multi-phase materials that are insoluble in the reaction medium and which have a Hammett acidity, denoted by $H_0$, of less than +2. As indicated in U.S. Pat. No. 5,387,720, which refers to the article by K. Tanabe et al. in "Studies in Surface Science and Catalysis", Vol. 51, 1989, chap. 1 and 2, the Hammett acidity is determined by amine titration using indicators or by adsorption of a base in the gas phase. The catalysts responding to the criteria of $H_0$ acidity of less than +2 may be chosen from natural or synthetic silaceous materials or acid zeolites; mineral supports, such as oxides, covered with mono-, di-, tri- or polyacidic inorganic acids; oxides or mixed oxides or else heteropolyacids.

Advantageously, the catalysts are chosen from zeolites, Nafion® composites (based on sulfonic acid of fluoro polymers), chlorinated aluminas, phosphotungstic and/or silicotungstic acids and acid salts, and various solids of the metal oxide type such as tantalum oxide $Ta_2O_5$, niobium oxide $Nb_2O_5$, alumina $Al_2O_3$, titanium oxide $TiO_2$, zirconia $ZrO_2$, tin oxide $SnO_2$, silica $SiO_2$ or silico-aluminate $SiO_2/Al_2O_3$, impregnated with acid functional groups such as borate $BO_3$, sulfate $SO_4$, tungstate $WO_3$, phosphate $PO_4$, silicate $SiO_2$, or molybdate $MoO_3$. According to data from the literature, these catalysts all have a Hammett acidity $H_0$ of less than +2.

The preferred catalysts are sulfated zirconias, phosphated zirconias, tungstated zirconias, silica zirconias, sulfated titanium or tin oxides, or phosphated aluminas or silicas.

These catalysts all have a Hammett acidity $H_0$ of less than +2, the acidity $H_0$ may then vary to a wide extent, down to values which may reach −20 in the reference scale with Hammett indicators. The table given on page 71 of the publication on acid/base catalysis (C. Marcilly), Vol. 1 in Editions Technip (ISBN No. 2-7108-0841-2) illustrates examples of solid catalysts within this acidity range.

It is possible to add molecular oxygen or a gas containing molecular oxygen for the glycerol dehydration step. The amount of oxygen is preferably chosen so as to be outside the explosive range at any point of the installation. The presence of oxygen makes it possible to limit the deactivation of the dehydration catalyst by coking. Furthermore, the addition of oxygen improves the yield of the reaction for numerous catalytic systems.

Preferably, the ammonia is introduced only in the second step.

The ammoxidation step of acrolein to acrylonitrile is then carried out over an ammoxidation catalyst at a temperature, in general, between 300° C. and 550° C. and, preferably, between 400° C. and 500° C., and under a pressure generally between 1 and 5 bar and, preferably, between 1 and 4 bar.

The composition of the reaction mixture, acrolein-ammonia-oxygen, may vary within wide limits and it is possible to use diluent gases that are inert under the reaction conditions such as helium, nitrogen or argon, or nitrogen from the air when the latter is used as an oxidizing agent.

The ammonia/acrolein and oxygen/acrolein molar ratios may vary within large proportions. The ammonia/acrolein molar ratio may vary between 1 and 1.5, and preferably between 1 and 1.2, and the oxygen/acrolein molar ratio may vary between 0.5 and 10 and preferably between 0.5 and 7.

As catalyst for the ammoxidation of acrolein, use will be made of an acid catalyst which is not saturated with ammonia at the reaction temperature. The catalyst may comprise one or more mixed oxides chosen, for example, from molybdenum, bismuth, iron, antimony, tin, vanadium, tungsten, antimony, zirconium, titanium, chromium, nickel, aluminum, phosphorus or gallium.

As ammoxidation catalysts which may be used, mention may especially be made of mixed oxides based on bismuth molybdate, mixed oxides containing at least Fe and Sb, or at least U and Sb, or at least Sn and Sb, or at least Mo and V, and/or W/Nb/Ti/Ta and/or Te/Sb/Bi, and also the oxynitrides containing at least Al and P.

One advantage of this embodiment consists of a better choice of the catalyst pair. Specifically, the dehydration reaction requires acid catalysts that can be inhibited by the presence of ammonia if they are too acidic. The separation of the two steps makes it possible to individually optimize the operation conditions of each of the two dehydration and ammoxidation reactions.

According to another preferred embodiment of the invention, illustrated by way of example in the appended single figure, the glycerol is first subjected to a step of dehydration to acrolein, and a partial condensation of the water and of the heavy byproducts originating from the dehydration step is carried out intermediarily.

The use of a prior step for the dehydration of the glycerol used in the form of an aqueous solution has the drawback of resulting in a stream that contains not only the acrolein produced and byproducts, but also a significant amount of water, which originates, on the one hand, from the glycerol solution and, on the other hand, from the water produced by the dehydration reaction.

The objective of the partial condensation step is to condense a portion of the water and of the products that have a higher boiling point than acrolein. It is therefore a simplified separation, which produces two streams, the first containing acrolein, and the light byproducts, such as acetaldehyde, propanaldehyde, acetone and optionally inert gases, CO and $CO_2$, the second, which is rich in water, containing the heavy byproducts such as phenol, hydroxypropanone, and the addition products of acrolein to glycerol (acetals), and products of the polycondensation of glycerol, cyclic or non-cyclic glycerol ethers, propionic acid, acrylic acid.

The partial condensation unit may be an absorption column that may or may not be coupled to a stripper, a heat exchanger, a condenser, a dephlegmator, and also any equipment well known to a person skilled in the art, and makes it possible to carry out a partial condensation of an aqueous stream. This unit may furthermore be used to reheat the aqueous glycerol solution, thus optimizing the energy cost of the installation.

After the intermediate condensation step, the acrolein-rich stream is sent over the ammoxidation catalyst, adding the ammonia necessary for the reaction and adjusting the partial pressures of the acrolein and oxygen reactants and optionally diluting the reaction gas with an inert gas.

By reference to FIG. 1, the glycerol is introduced as (1), in the form of an aqueous solution, into a first dehydration reactor (10). Molecular oxygen (2) is also introduced, for example in the form of air or in the form of air enriched with or depleted in molecular oxygen. The dehydration reaction is carried out in the gas phase in the reactor (10) in the presence of a dehydration catalyst, at a temperature between 250° C. and 350° C. and under a pressure between 1 and 5 bar.

The gas stream, on exiting the reactor (10), is composed of a mixture comprising acrolein, water, unconverted glycerol and byproducts. The byproducts are especially hydroxypropanone, propanaldehyde, acetaldehyde, acetone, phenol, addition products of acrolein to glycerol, polycondensation products of glycerol, cyclic or non-cyclic glycerol ethers.

This stream is sent to a condensation unit (11) which separates, on the one hand, a mixture (3) rich in water that contains the heavy byproducts, and, on the other hand, a stream (4) rich in acrolein that contains the light byproducts, such as acetaldehyde, propanaldehyde, acetone and optionally inert gases, CO and $CO_2$.

All or part of the stream (3) is sent either to a rectification column for the purpose of recovering the light fraction which might be absorbed in this stream, or to a wastewater treatment plant. It may also be sent to a thermal oxidizer, or else a portion of this stream is recycled in order to dilute the glycerol to the desired concentration.

The stream (4), which is rich in acrolein and free of the heavy byproducts and of most of the water is sent to the ammoxidation reactor (12) that comprises a fixed bed of the ammoxidation catalyst for the acrolein.

The reaction is carried out in the presence of molecular oxygen (6) which may be in the form of air or in the form of air enriched with or depleted in molecular oxygen, at a content ranging from 3 to 20 vol %, relative to the incoming stream, and in the presence of a gas mixture (5) comprising inert gases and ammonia. The inert gases necessary for the process may optionally be completely or partly composed of gases (8) obtained at the top of the absorption column (13).

The ammoxidation reaction is carried out at a temperature between 400° C. and 500° C., and under a pressure between 1 and 5 bar.

The effluent (7) from the ammoxidation step which is rich in acrylonitrile is then purified in a separation unit (13) in order to separate, on the one hand, the light products (8) and the unconverted acrolein, and, on the other hand, the acrylonitrile (9), which may still contain traces of heavy byproducts.

According to another embodiment of the invention, the ammoxidation reaction of the glycerol is carried out in the presence of a gas that contains propylene. The propylene-containing gas may be co-fed with the glycerol, or it may be fed after the glycerol dehydration reaction.

According to another embodiment of the invention, the ammoxidation reaction of the glycerol is carried out in the presence of a thermal ballast, such as for example propane or a gas that contains propane, methane, ethane or $CO_2$.

The thermal ballast is a heat transfer fluid, which may be used to provide the heat necessary for the dehydration reaction, but also to take away the heat produced during the ammoxidation reaction. The thermal ballast may be introduced together with the glycerol, or when the dehydration and ammoxidation steps are separate, it may be introduced between these steps. The thermal ballast, such as propane, is optionally recovered and recycled.

The products from the reaction may be recovered in the effluent gases by any suitable means. For example, the effluent gases may pass into a condenser that contains dilute sulfuric acid in order to neutralize the unconverted ammonia. The gases may then pass through a cooled absorbent column in order to condense the acrylonitrile, the acetonitrile and the hydrocyanic acid. It is then possible to isolate the acrylonitrile from the byproducts by successive distillation.

Via the process of the invention, it is possible to obtain high-purity acrylonitrile with a good productivity, while reducing the dependence on a fossil resource such as propylene. The acrylonitrile which may be obtained according to this process contains $^{14}C$, advantageously the acrylonitrile contains $^{14}C$ at a content higher than $10^{-11}$% relative to the total carbon, which could be certified by measurement according to one of the methods described in the standard ASTM D6866-06.

The acrylonitrile which may be obtained according to the process of the invention is used for preparing, in particular, adiponitrile, a precursor of nylon, synthetic polymers such as acrylic fibers, synthetic rubber, elastomers, or resins such as copolymers of acrylonitrile, butadiene and styrene (ABS resins) or copolymers of styrene and acrylonitrile (SAN resins). The products thus obtained contain organic carbon derived from a renewable resource that corresponds to the concept of green chemistry.

The examples below illustrate the present invention without however limiting the scope thereof.

EXAMPLES

Example 1

Figure 2:
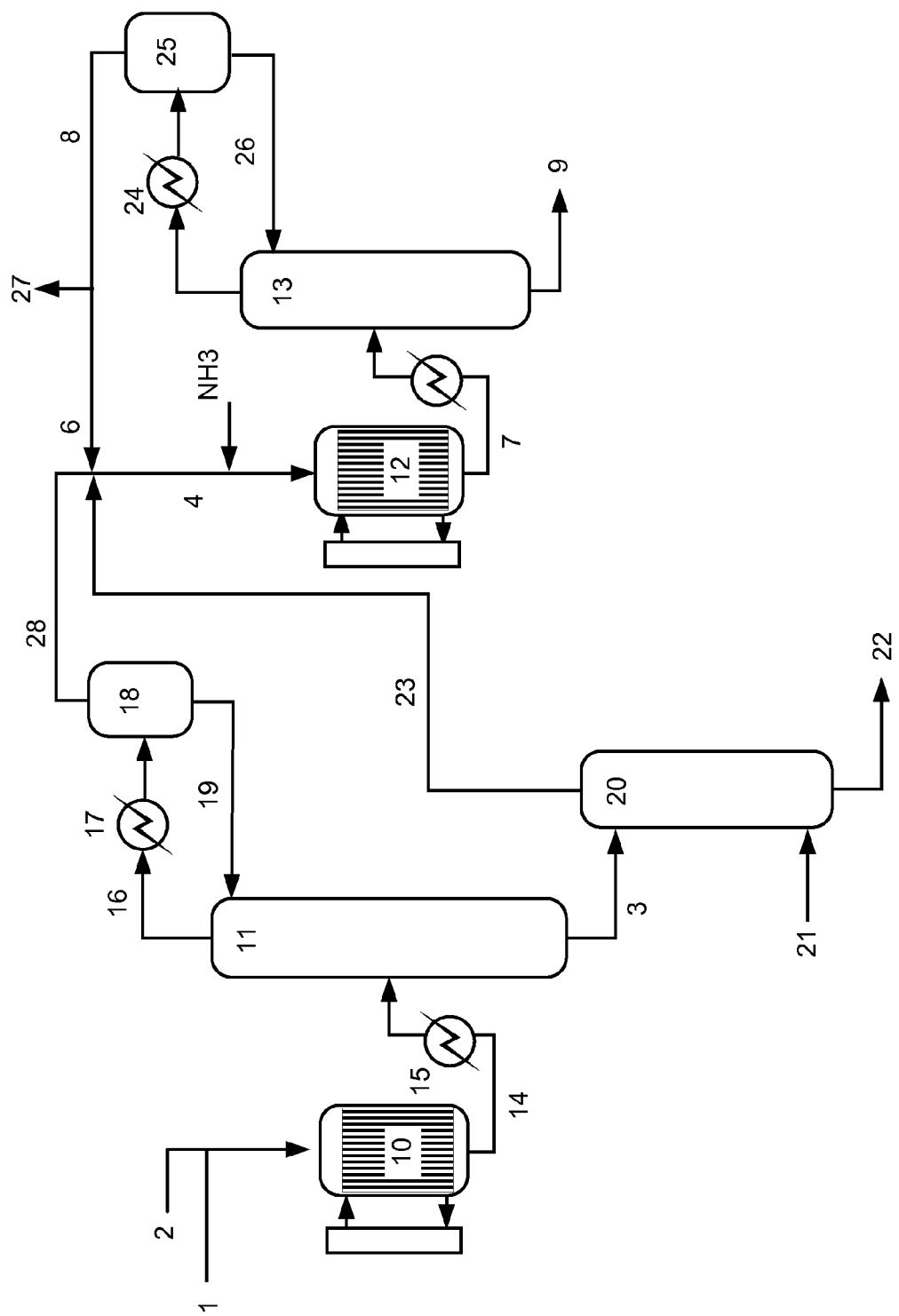
FIG. 2 is a schematic of a variation of the process of FIG. 1 wherein partial condensation takes place in an absorption column coupled to a stripper, a heat exchanger, and a condenser.

With Reference to FIG. 2

A simulation using ASPEN software was used to illustrate the process according to the invention. The values are given in kmol/hour. For the sake of clarity, only the main constituents are indicated.

A gas stream at 331° C. and at 2.0 bar (188 kmol/h glycerol, 963 kmol/h water, 426 kmol/h nitrogen, 113 kmol/h oxygen) is sent into a fixed-bed multitubular reactor (10) containing a heterogeneous dehydration catalyst coupled to a molten salt bath. A gas stream (14) at 320° C. and at 1.7 bar (1336 kmol/h water, 426 kmol/h nitrogen, 78 kmol/h oxygen, 147 kmol/h acrolein, 19 kmol/h acetaldehyde, 25 kmol/h CO, 13 kmol/h $CO_2$) exits this reactor. This stream is cooled to 151° C. in a heat exchanger (15) and sent to the bottom of an absorption column (11) that comprises 4 theoretical plates. The gas stream (16) that exits at 102° C. at the top of this absorption column is sent to a partial condenser (17) which cools it to 79° C., then to a flash chamber (18) that separates the gas phase (28) from the liquid phase (19). This liquid phase (19) is sent back to the top of the absorption column (11). At the bottom of the absorption column, a liquid phase (3) at 103° C. (1067 kmol/h water, 4 kmol/h acetic acid, 4 kmol/h formic acid) is drawn off. This liquid phase (3) is sent to the top of a stripping column (20) comprising 8 plates, into the bottom of which air (21) is injected at 90° C. and at 1.7 bar. At the bottom of this stripping column, an aqueous stream (22) (55° C., 976 kmol/h water, 4 kmol/h acetic acid, 4 kmol/h formic acid) is recovered. The gas stream (23) recovered at the top of the stripping column is mixed with the gas phase (24) from the flash chamber described previously (79° C., 426 kmol/h $N_2$, 145 kmol/h acrolein, 78 kmol/h oxygen, 270 kmol/h water, 18 kmol/h acetaldehyde, 25 kmol/h carbon monoxide, 13 kmol/h carbon dioxide) and with a gas stream (6) (923 kmol/h nitrogen, 38 kmol/h oxygen, 134 kmol/h water, 41 kmol/h carbon dioxide, 53 kmol/h carbon monoxide) to which a stream of ammonia (178 kmol/h) is added. The mixture is reheated to 300° C., then injected into a second multitubular reactor (12) comprising an armoxidation catalyst. At the outlet of this reactor, a gas stream (7) at 1.4 bar (2030 kmol/h nitrogen, 830 kmol/h water, 118 kmol/h acrylonitrile, 52 kmol/h oxygen, 155 kmol/h carbon dioxide, 85 kmol/h carbon monoxide) is obtained. This stream is cooled to 157° C. then injected into the bottom of the absorption column (13). At the top of this column, the gas stream is partially condensed in the heat exchanger (24), then sent to a separator pot (25) which produces a liquid phase (26) and a gas phase (8) (nitrogen, oxygen, water, carbon dioxide, carbon monoxide). The liquid phase (26) is sent back to the column (13). The gas phase (8) is partially recycled upstream of the reactor (12) via the stream (6). At the bottom of the absorption column (13) a concentrated stream (9) of acrylonitrile (116 kmol/h acrylonitrile, 587 kmol/h water and other byproducts) is obtained.

It should be noted that the process makes it possible to eliminate, in the aqueous phase (22), certain impurities produced in the dehydration reactor (10): for example the flow rates of hydroxypropanone and of acetic acid in the gas stream exiting the dehydration reactor (10) are respectively 1 and 4 kmol/h. They are respectively 0.02 and 0.3 kmol/h at the inlet of the oxidation reactor (12).

In the examples that follow, the conversion of glycerol, the acrolein selectivity and the yields of various products are defined as follows:

Conversion of glycerol (%)=100−number of moles of glycerol remaining/number of moles of glycerol introduced.

Yield of acrolein (%)=number of moles of acrolein produced/number of moles of glycerol introduced.

Acrolein selectivity (%)=100×number of moles of acrolein produced/number of moles of glycerol reacted.

The yield of acetone or hydroxypropanone is calculated in the same way as for the yield of acrolein.

Yield of acetaldehyde (%)=⅔×number of moles of acetaldehyde produced/number of moles of glycerol introduced.

Yield of phenol (%)=2×number of moles of phenol produced/number of moles of glycerol introduced.

All the results are expressed in molar percent relative to the glycerol introduced.

Example 2

Acrolein Preparation

A tubular reactor composed of a tube having a length of 35 cm and an internal diameter of 22 mm is used to carry out the dehydration reaction of glycerol in the gas phase at atmospheric pressure. This reactor is placed in a heated chamber maintained at the reaction temperature, which is 300° C., unless otherwise indicated. The catalyst used is milled and/or pelleted in order to obtain particles of 0.5 to 1.0 mm. 10 ml of catalyst are charged in the reactor to form a catalytic bed having a length of 5 cm. This bed is brought to the reaction temperature for 5 to 10 minutes before the introduction of the reactants. The reactor is fed with a 20 wt % aqueous solution of glycerol with an average feed rate of 12 ml/h, and with a flow rate of 0.8 l/h of molecular oxygen for the examples according to the invention. In this case, the relative $O_2$/vaporized glycerol/water vapor proportion is 6/4.5/89.5. The aqueous glycerol solution is vaporized in the heated chamber, then passes over the catalyst. The calculated contact time is of the order of 2.9 s. After reacting, the products are condensed in a trap cooled with crushed ice.

The total mass of products at the inlet and the outlet is measured, which makes it possible to carry out a mass balance. Similarly, the products formed are analyzed by chromatography.

The products thus quantified are unreacted glycerol, the acrolein formed, and the byproducts such as hydroxypropanone, acetaldehyde, propanaldehyde, acetone and phenol.

In this example, the catalyst (10 ml) tested is a tungstated zirconia (90.7% $ZrO_2$-9.3% $WO_3$) from Daiichi Kigenso (supplier reference H1417). The catalyst is characterized by an ignition loss at 1000° C. of 1.75% and a specific surface area of 47.4 $m^2$/g (BET, 1 point). The results are indicated in the following table:

|  | Total glycerol introduced (g) | |
| --- | --- | --- |
|  | 21 | 33 |
| Catalyst | Tungstated zirconia 17 g | |
| Conversion of glycerol | 100 | 100 |
| Yield of acrolein | 54.9 | 53.0 |
| Acrolein selectivity | 55 | 53 |
| Yield of hydroxypropanone | 0.0 | 0.0 |
| Yield of acetaldehyde | 9.8 | 8.7 |
| Yield of propanaldehyde | 2.1 | 1.4 |
| Yield of acetone | 0.1 | 0.1 |
| Yield of phenol | 0.0 | 0.0 |
| Material balance (mass collected/mass introduced) | 97.2 | 97.9 |

The acrolein produced contains neither hydroxypropanone nor phenol.

Example 3

Synthesis of Acrylonitrile

A pyrex reactor is charged with a catalyst bed. The reactor is equipped with a frit in order to retain the catalyst. The reactor is first charged with a mass of 6.578 g of catalyst for the oxidation of propylene to acrolein which is produced by Nippon Shokubai with reference ACF4, used in this example as an ammoxidation catalyst although it is not optimized for this reaction, diluted with 7 ml of silicon carbide having a particle size of 0.125 mm. Charged next are beds of silicon carbide having a particle size of 0.125 mm in an amount of 2 ml, and then 7 ml of 0.5 mm. And finally the reactor is completed with 1.19 mm silicon carbide up to the top of the reactor.

The reactor is then connected to the test installation. The temperature of the catalyst is regulated at 420° C. and the HSV is adjusted to 1200 $h^{-1}$.

The reactor is fed with a gas mixture of 4.5% acrolein/8.7% oxygen/5.4% ammonia/(remainder) helium-krypton/15% water. The helium-krypton gas mixture contains 4.92% krypton which serves as an internal standard. Use is made of the water-acrolein mixture from example 2, vaporized upstream of the reactor, after concentration.

The effluents are collected at the outlet of the reactor by a ice-cooled trap and the acrylonitrile produced is assayed by chromatographic analysis.

The yield of acrylonitrile is 60%.

The invention claimed is:

1. A process for the manufacture of acrylonitrile comprising:
   a) introducing in a first dehydration reactor, glycerol in the form of an aqueous solution, and molecular oxygen;
   a) dehydrating glycerol in the gas phase to acrolein in the presence of a first acid catalyst at a temperature ranging from 150° C. to 500° C., and a pressure between 1 and 5 bar, forming a gas stream comprising acrolein, water, unconverted glycerol and by-products;
   b) sending the said gas stream to a condensation unit which separates, on the one hand, a mixture rich in water that contains the heavy by-products, and, on the other hand, a stream rich in acrolein that contains the light by-products and optionally inert gases;
   c) recycling a portion of the separated stream rich in water in order to dilute the glycerol to the desired concentration and using the condensation unit to reheat the aqueous glycerol solution;
   d) sending the separated stream rich in acrolein to an ammoxidation reactor comprising a fixed bed of an ammoxidation catalyst for the acrolein which is not saturated with ammonia at the reaction temperature;
   e) carrying out the ammoxidation reaction in the presence of molecular oxygen at a content ranging from 3 to 20 vol %, relative to the incoming stream, and in the presence of a gas mixture comprising inert gases and ammonia, the ammonia/acrolein molar ratio being between 1 and 1.5, at a temperature between 400° C. and 500° C., and under a pressure between 1 and 5 bar, forming an effluent rich in acrylonitrile;
   f) purifying said effluent in a separation unit in order to separate, on the one hand, the light products and the unconverted acrolein, and on the other hand, acrylonitrile;

g) recycling partly the gases obtained at the top of the separation unit of the step f), in the ammoxidation reactor at the step e).

2. The process of claim 1, wherein said aqueous solution comprising glycerol has a concentration of glycerol ranging from 10% to 100%.

3. The process of claim 1, wherein the ammoxidation reaction is carried out in the presence of a gas comprising propylene.

4. The process of claim 1, wherein the ammoxidation reaction is carried out in the presence of a thermal ballast.

5. The process of claim 1, wherein said dehydration step is carried out at a temperature between 400° C. and 500° C.

6. The process of claim 1, wherein said dehydration step is carried out at a temperature between 250° C. and 350° C.

7. The process of claim 1, wherein said first acid catalyst is selected from the group consisting of: zeolites, Nafion® composites, chlorinated aluminas, phosphotungstic and/or silicotungstic acids and acid salts, metal oxides, and mixtures thereof.

8. The process of claim 1, wherein said first acid catalyst is selected from the group consisting of: sulfated zirconias, phosphated zirconias, tungstated zirconias, silica zirconias, sulfated titanium, tin oxides, phosphated aluminas, silicas, and mixtures thereof.

9. The process of claim 1, wherein said ammoxidation reaction is carried out under a pressure between 1 and 4 bar.

10. The process of claim 1, wherein said ammonia/acrolein molar ratio is between 1 and 1.2.

11. The process of claim 1, wherein said ammoxidation catalyst comprises mixed oxides of molybdenum, bismuth, iron, antimony, tin, vanadium, tungsten, antimony, zirconium, titanium, chromium, nickel, aluminum, phosphorus, and/or gallium.

12. The process of claim 1, wherein said ammoxidation catalyst comprises oxynitrides containing at least Al and P, mixed oxides based on bismuth molybdate, mixed oxides containing at least Fe and Sb, mixed oxides containing at least U and Sb, mixed oxides containing at least Sn and Sb, mixed oxides containing at least Mo and V, mixed oxides containing at least W, Nb, Ti, and Ta, and/or mixed oxides containing at least Te, Sb, and Bi.

* * * * *